United States Patent
Kalhor et al.

(10) Patent No.: US 11,732,258 B2
(45) Date of Patent: Aug. 22, 2023

(54) ENGINEERED GUIDE RNA SEQUENCES FOR IN SITU DETECTION AND SEQUENCING

(71) Applicant: President and Fellows of Harvard College, Cambridge, MA (US)

(72) Inventors: Reza Kalhor, East Boston, MA (US); Prashant G. Mali, La Jolla, CA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 192 days.

(21) Appl. No.: 16/346,569

(22) PCT Filed: Nov. 1, 2017

(86) PCT No.: PCT/US2017/059549
§ 371 (c)(1),
(2) Date: May 1, 2019

(87) PCT Pub. No.: WO2018/085414
PCT Pub. Date: May 11, 2018

(65) Prior Publication Data
US 2019/0264202 A1    Aug. 29, 2019

Related U.S. Application Data

(60) Provisional application No. 62/428,010, filed on Nov. 30, 2016, provisional application No. 62/416,401, filed on Nov. 2, 2016.

(51) Int. Cl.
| | | |
|---|---|---|
| *C12N 15/00* | (2006.01) |
| *C12N 15/11* | (2006.01) |
| *C12N 15/10* | (2006.01) |
| *C12Q 1/6853* | (2018.01) |
| *C12N 9/22* | (2006.01) |
| *C12N 15/113* | (2010.01) |

(52) U.S. Cl.
CPC ............... *C12N 15/11* (2013.01); *C12N 9/22* (2013.01); *C12N 15/10* (2013.01); *C12N 15/1096* (2013.01); *C12N 15/113* (2013.01); *C12Q 1/6853* (2013.01); *C12N 2310/20* (2017.05); *C12N 2310/3519* (2013.01); *C12N 2310/531* (2013.01)

(58) Field of Classification Search
CPC C12N 15/1096; C12N 2310/20; C12N 15/11; C12N 9/22; C12N 15/10; C12N 15/113; C12N 2310/3519; C12N 2310/531; C12Q 1/6853
See application file for complete search history.

(56) References Cited

U.S. PATENT DOCUMENTS

| | | | |
|---|---|---|---|
| 2016/0215275 A1* | 7/2016 | Zhong | C12N 15/111 |
| 2016/0237456 A1 | 8/2016 | Church et al. | |
| 2016/0251648 A1* | 9/2016 | Wang | C12N 15/113 506/10 |
| 2016/0289675 A1 | 10/2016 | Ryan et al. | |
| 2019/0330661 A1* | 10/2019 | Zhang | C12N 15/907 |

FOREIGN PATENT DOCUMENTS

| | | | | |
|---|---|---|---|---|
| CN | 101970685 | * | 2/2011 | ............. A61P 35/02 |
| WO | WO-2013176772 A1 | * | 11/2013 | ........... C12N 15/113 |
| WO | 2015/168404 A1 | | 11/2015 | |

OTHER PUBLICATIONS

Translation of paragraph 0274 for CN 101970685 (Year: 2011).*
Kalhor, Mali, and Church entitled "Rapidly evolving homing CRISPR barcodes" (bioRxiv pages published online May 27, 2016). (Year: 2016).*

* cited by examiner

*Primary Examiner* — Catherine S Hibbert
(74) *Attorney, Agent, or Firm* — Banner & Witcoff, Ltd.

(57) ABSTRACT

A functional engineered guide RNA sequence is provided including a spacer sequence and a scaffold sequence, wherein the scaffold sequence includes a primer binding site for reverse transcription.

12 Claims, 7 Drawing Sheets
(6 of 7 Drawing Sheet(s) Filed in Color)
Specification includes a Sequence Listing.

Figure 4

>Design 0 (standard gRNA)
5' NNNNNNNNNNNNNNNNNNNNGTTTTAGAGCTAGAAATAGCAAGTTAAAATAAGGCTAGTCCGTTATCAACTTGAAAAAGTGGCACCGAGTCGGTGC*CACTGTTGTCTTATACCAACTT TCC* -3'

>Design 1
5' NNNNNNNNNNNNNNNNNNNNGTTTTAGAGCTAATTA*CACTGTTGTCTTATACCAACTT*AAGTGGCACCGAGTCCGTTATCAACTTGAAAAAGTTAAAATAAGGCTA*TCCT*AATTAGCAAGTTAAAATAAGGCTAGTCCGTTATCAACTTGAAAAAGTGGCACCGAGTCGGTGC-3'

>Design 2
5' NNNNNNNNNNNNNNNNNNNNGTTTTAGAGCTAGAAATAGCAAGTTAAAATAAGGCTA*CCAACTT*CCTAATAAGTGGCACCGAGTCCGTTATCAACTTATTA*CACTGTTGTCTTATACCAACTT*TCGGTGC-3'

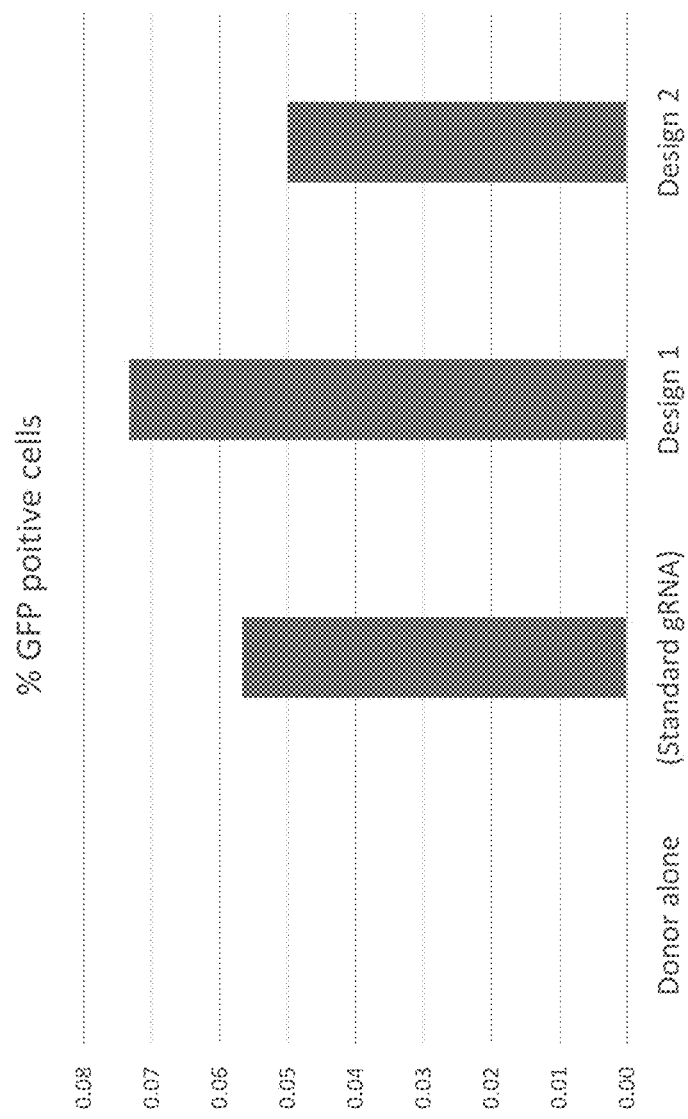

ENGINEERED GUIDE RNA SEQUENCES FOR IN SITU DETECTION AND SEQUENCING

RELATED APPLICATION DATA

This application is a National Stage Application under 35 U.S.C. 371 of co-pending PCT application PCT/US17/59549 designating the United States and filed Nov. 1, 2017; which claims the benefit of U.S. provisional application No. 62/428,010 filed on Nov. 30, 2016 and U.S. Provisional Application No. 62/416,401 filed on Nov. 2, 2016 each of which are hereby incorporated by reference in their entireties.

STATEMENT OF GOVERNMENT INTERESTS

This invention was made with government support under MH103910 and HG005550 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 3, 2020, is named 010498_01243_US_SL.txt and is 7,362 bytes in size.

BACKGROUND

CRISPR-Cas forms the basis of numerous technologies used for gene therapy, genomic screens, modification of transcription, drug screens, etc. CRISPR comprises Cas9 nuclease which associates with a guide RNA (gRNA) molecule to target a DNA locus for digestion. The sequence of a gRNA region, called the spacer, determines the identity of the target locus. As a result, multiple targets can be affected with Cas9 by using multiple gRNAs with different spacer sequences. Furthermore, modified Cas9 proteins have been created that modify the target locus in ways other than digestions, such as creating nicks and enhancing or repressing expression. For the gRNA, a few modified versions designed for modulating CRISPR function have also been created. These modifications have expanded the versatility and application of CRISPR technology. However, methods for identifying spacer sequences of guide RNA within a cell would be advantageous.

SUMMARY

The present disclosure provides methods and materials for identifying and/or sequencing a guide RNA spacer sequence within a cell using sequencing methods, such as in situ sequencing methods, such as fluorescent in situ sequencing methods generally known to those of skill in the art. According to one aspect, the guide RNA sequence includes a spacer sequence which is complementary to a target nucleic acid sequence, known as a protospacer sequence. A guide RNA sequence also includes a tracr mate sequence connected to the spacer sequence. The tracr mate sequence may be referred to herein as a scaffold sequence. The combination of a spacer sequence and a tracr mate sequence may be referred to in the art as a crRNA. A guide RNA also includes a tracrRNA sequence which hybridizes to the tracr mate sequence. The tracr mate sequence and the tracrRNA sequence may be connected, such as by a linker sequence and the combination may be referred to as a fusion and may also be referred to as a scaffold sequence. The scaffold sequence is generally the RNA sequence that is attached to the 3' end of the spacer sequence. The scaffold sequence may also have a poly U or poly T tail at the 3' end of the scaffold sequence and may include one or more, two or more or three or more or a plurality of stem and loop structures. A DNA binding protein interacts with the scaffold sequence of the guide RNA to colocalize at the protospacer sequence of a target nucleic acid. The spacer sequence hybridizes to the protospacer sequence of the target nucleic acid. The DNA binding protein modulates the target nucleic acid sequence through binding of the co-localization complex, through enzymatic activity of the DNA binding protein or through an effector moiety bound to the DNA binding protein or the guide RNA or both as further described herein According to one aspect, the scaffold sequence includes a reverse transcription primer binding site sequence or docking site sequence at a location within the scaffold sequence maintaining the function or ability of the guide RNA sequence to bind to the protospacer and also to form a colocalization complex with the DNA binding protein. In this manner the guide RNA including the reverse transcription primer binding site sequence or docking site sequence within or art of the scaffold sequence is referred to as being "functional." Stated differently, the guide RNA retains its function even though it includes the reverse transcription primer binding site sequence or docking site sequence. Further, the reverse transcription primer binding site sequence or docking site sequence is at a location within the scaffold sequence which facilitates reverse transcription of the spacer sequence into a cDNA sequence. According to one aspect, the reverse transcription primer binding site sequence or docking site sequence is positioned at a location proximate to the spacer sequence. According to one aspect, the reverse transcription primer binding site sequence or docking site sequence is positioned at a location proximate to the spacer sequence so as to minimize the amount of the scaffold sequence, i.e. number of nucleotides, being reverse transcribed while maintaining the function of the guide RNA sequence. According to one aspect, the reverse transcription primer binding site sequence or docking site sequence is located within or is part of or comprises or is a linker sequence (i.e., the reverse transcription primer binding site may be the linker sequence itself or it may include additional nucleotides which comprise the linker sequence but are not part of the reverse transcription primer binding site) of a stem loop structure of the scaffold sequence. In this manner, the spacer sequence of a functioning guide RNA sequence can be identified using reverse transcription, amplification and sequencing methods known to those of skill in the art.

In accordance with certain examples, methods of sequencing nucleic acid in situ are provided. General sequencing methods known in the art, such as sequencing by extension with reversible terminators, fluorescent in situ sequencing (FISSEQ), pyrosequencing, massively parallel signature sequencing (MPSS) and the like (described in Shendure et al. (2004) Nat. Rev. 5:335, incorporated herein by reference in its entirety), are suitable for use, in the present methods of identifying and sequencing the spacer sequence of the guide RNA. A matrix may be used with the methods, as is known in the art. Reversible termination methods use step-wise sequencing-by-synthesis biochemistry that couple reversible termination and removable fluorescence (Shendure et al. supra and U.S. Pat. Nos. 5,750,341 and 6,306,597, incorporated herein by reference.) FISSEQ is a method whereby DNA is extended by adding a single type of fluorescently-labelled nucleotide triphosphate to the reaction mixture, washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described further in Mitra et al. (2003) Anal. Biochem. 320:55, which is incorporated herein by reference in its entirety for all purposes. Pyrosequencing is a method in which the pyrophosphate (PPi) is released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) Science 281:363, incorporated herein by reference in its entirety for all purposes. MPSS utilizes ligation-based DNA sequencing simultaneously on microbeads. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al. (2000) Nat. Biotech. 18:630, incorporated herein by reference in its entirety for all purposes. According to certain aspects, the nucleic acids within the matrix can be interrogated using methods known to those of skill in the art including fluorescently labeled oligonucleotide/DNA/RNA hybridization, primer extension with labeled ddNTP, sequencing by ligation and sequencing by synthesis. Ligated circular padlock probes described in Larsson, et al., (2004), Nat. Methods 1:227-232 can be used to detect multiple sequence targets in parallel, followed by either sequencing-by-ligation, -synthesis or -hybridization of the barcode sequences in the padlock probe to identify individual targets. Methods may be used that include the process of creating a matrix of the guide RNA sequences within cells in situ, followed by amplifying the guide RNA sequences, in situ, co-polymerizing the amplicons in situ, covalently attaching the amplicons to the matrix material, interrogating or otherwise identifying or sequencing the spacer sequence of the guide RNA sequences. According to certain aspects, FISSEQ methods and materials useful in the practice of the methods described herein are provided in Lee et al., Nature Protocols, vol. 10, No. 3 (2015) pp. 442-458, Lee et al., Science 343, 1360-1363 (2014) and Supplementary Materials published 27 Feb. 2014 on Science Express DOI: 10.1126/scienmce.1250212 each of which are hereby incorporated by reference in its entirety.

According to one aspect, the spacer sequence is identified using fluorescent in situ sequencing. In an exemplary aspect, Fluorescent in situ sequencing (FISSEQ) is a technology that sequences RNA molecules inside a cell without extraction, thus identifying the location of RNA molecules in their corresponding cells, tissues, or organs. In the standard FISSEQ protocol, cells are fixed using formalin and permeabilized. Reverse-transcription is then carried out using a random hexamer primer that has a universal adaptor sequence (5P-universal_adaptor-NNNNNN) in the presence of aminoallyl-dUTP. Nascent cDNA strands are crosslinked by treatment with BS(PEG)9 and the original template RNA is degraded by RNaseA and RNaseH treatment. cDNA is then circularized using CircLigaseII enzyme. Rolling circle amplification (RCA) is carried out with Phi29 polymerase using a primer that identifies the universal adaptor in the presence of aminoallyl-dUTP. Nascent amplicons or 'rolonies' are fixed in place by treatment with BS(PEG)9. Finally, all amplicons/rolonies are sequenced with a fluorescent sequencing chemistry, such as SoLiD or Illumina to decipher the sequence of the amplified RNA molecules.

For purposes of the present disclosure, the protospacer sequence may be referred to as the double stranded sequence targeted by the guide RNA spacer sequence. While the guide RNA spacer sequence will bind to one strand of the protospacer sequence, i.e. the complement of the guide RNA spacer, the sequence of the guide RNA spacer may be described with respect to either strand of the protospacer sequence. For example, the guide RNA spacer sequence may be described as being complementary to one strand of the protospacer sequence while the guide RNA spacer sequence may be described as being identical to the other strand of the protospacer sequence. Accordingly, guide RNA spacer sequences may be described as being designed with respect to either strand. Should a guide RNA spacer sequence be described as being identical to a protospacer sequence, it is to be understood that the guide RNA spacer sequence is being designed with respect to the protospacer strand to which it will not bind. In this manner, the resulting guide RNA spacer sequence will bind to the other protospacer strand to which it is complementary.

The DNA binding protein may be an RNA guided DNA binding protein to target and form a co-localization complex with the target nucleic acid including the protospacer sequence. The RNA guided DNA binding protein may be enzymatically active or nuclease null, but may have an effector group bound thereto. The guide RNA may have an effector group bound thereto. The formation of a colocalization complex results in modulation of the target nucleic acid sequence based on the binding and formation of the colocalization complex or based on the enzymatic function of the DNA binding protein itself, i.e. cutting or nicking, or any effector group, i.e. cutting or nicking enzyme, transcriptional modulator, detectable moiety, etc., that may be bound to either the DNA binding protein or guide RNA or both.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIG. 4 depicts exemplary nonlimiting embodiments of engineered guide RNA sequences (Design 0 (SEQ ID NO: 22), Design 1 (SEQ ID NO: 14) and Design 2 (SEQ ID NO: 17)) relating to the sequence shown in FIG. 3 where blue bases mark the spacer, which can vary, and purple bases mark the scaffold. The underline marks the engineered stem loop with the bold-italicized sequence within the underline marking the RT primer docking site comprising the linker sequence of a stem loop position. The bold "GAAA" sequence marks the linker or loop of a stem loop position.

FIG. 5 depicts results of a HR-based assay to evaluate functionality of Design 1 and Design 2 FISSEQable gRNAs, i.e. the structure of the spacer sequence of the guide RNA sequence may be determined using FISSEQ. A genomically integrated GFP coding sequence is disrupted by the insertion of a stop codon and a 68-bp genomic fragment from the AAVS1 locus. Restoration of the GFP sequence by HR with an appropriate donor sequence results in GFP+ cells that can be quantified by FACS. AAVS1 locus contains a site known as T1 which matches the spacer sequence of the gRNAs. Bar graphs depict HR efficiencies induced by standard, Design1, and Design2 guide RNAs, as measured by FACS. Data are represents triplicates.

DETAILED DESCRIPTION

Figure 1:
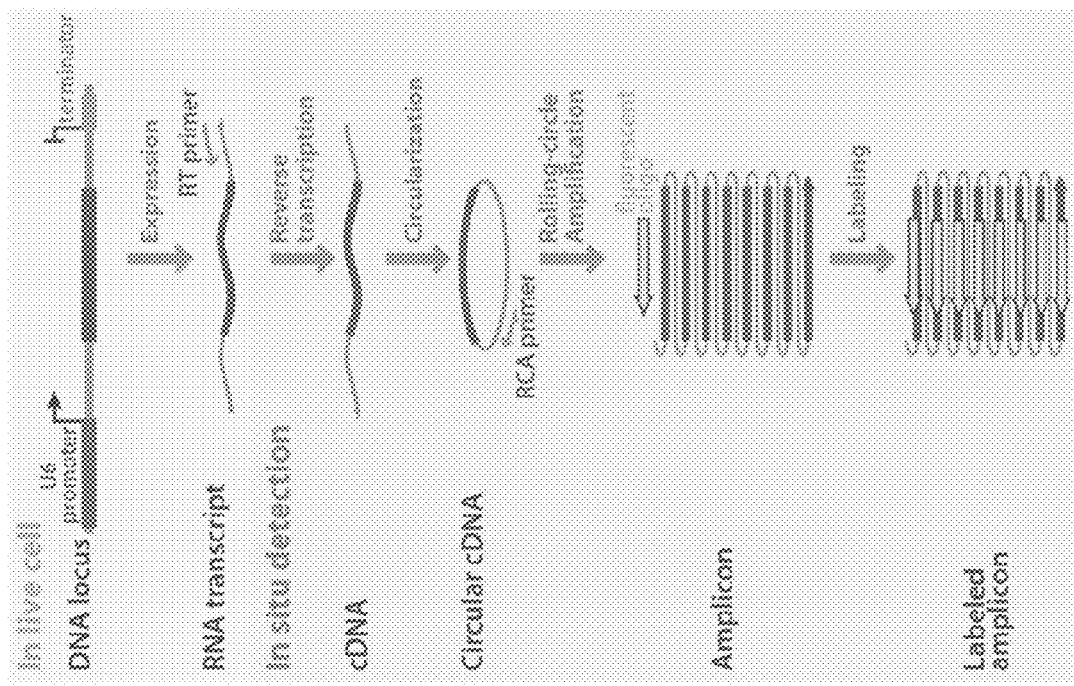
FIG. 1 is a schematic showing an exemplary in situ amplification and detection assay based on FIS SEQ. A DNA locus expressing a gRNA (purple) under the U6 promoter (brown) is introduced into cells. The construct also contains designed primer binding sites both downstream and upstream of the gRNA in grey-colored regions. A terminator (light brown) is placed after the second primer binding region. Cells containing this locus, and thus expressing its RNA transcript, are fixed for in situ amplification and detection. In the fixed cells, the RNA transcript is reverse-transcribed using a locus-specific RT (reverse-transcription) primer to obtain a cDNA which is then circularized. The circular cDNA is amplified by the rolling circle amplification (RCA) using a second locus-specific RCA primer, producing a concatemerized amplicon that is confined to a small space in the hydrogel matrix of the experiment. The amplicon is then labeled by a fluorescent oligonucleotide.

Embodiments of the present disclosure are directed to functional guide RNA sequences which include a reverse transcription primer binding site sequence or docking site sequence at a location within the scaffold sequence maintaining the function or ability of the guide RNA sequence to bind to the protospacer and also to form a colocalization complex with the DNA binding protein. Further, the reverse transcription primer binding site sequence or docking site sequence is at a location within the scaffold sequence which facilitates reverse transcription of the spacer sequence into a cDNA sequence. According to one aspect, the reverse transcription primer binding site sequence or docking site sequence is positioned at a linker sequence, i.e. loop sequence, of a hairpin structure of the guide RNA scaffold sequence. The reverse transcription primer binding site sequence or docking site sequence is used in a method of in situ sequencing of the spacer sequence, and may also include a portion of the scaffold sequence, using methods described herein and known to those of skill in the art.

Combining engineered guide RNA molecules as described herein with an RNA-guided DNA binding protein, such as a Cas protein of a CRISPR system as is known in the art, and a target nucleic acid sequence including a protospacer sequence results in co-localization of the guide RNA and the RNA-guided DNA binding protein with the target nucleic acid sequence. If the RNA-guided DNA binding protein is a nuclease or a nickase, the RNA-guided DNA binding protein will cut or nick the target nucleic acid. According to one aspect, the RNA-guided DNA binding protein includes an effector group, such as a transcriptional modulator, such as a transcriptional activator or transcriptional repressor which modulates expression of the target nucleic acid. The guide RNA and/or RNA guided DNA binding protein may be exogenous or foreign or engineered or nonnaturally occurring. According to certain aspects, the cell includes a naturally occurring Cas protein. According to certain aspects, the guide RNA and the Cas protein which interacts with the guide RNA are foreign to the cell into which they are introduced or otherwise provided. According to this aspect, the guide RNA and the Cas protein are nonnaturally occurring in the cell in which they are introduced, or otherwise provided. To this extent, cells may be genetically engineered or genetically modified to include the CRISPR/Cas systems described herein.

According to certain aspects, the Cas protein may be delivered directly to a cell as a native species by methods known to those of skill in the art, including injection or lipofection, or as translated from its cognate mRNA, or transcribed from its cognate DNA into mRNA (and thereafter translated into protein). Cas DNA, i.e. DNA encoding a Cas protein and mRNA may be themselves introduced into cells through electroporation, transient and stable transfection (including lipofection) and viral transduction or other methods known to those of skill in the art. According to certain aspects, the guide RNA may be delivered directly to a cell as a native species by methods known to those of skill in the art, including injection or lipofection, or as transcribed from its cognate DNA, with the cognate DNA introduced into cells through electroporation, transient and stable transfection (including lipofection) and viral transduction. One or more, two or more, or three or more nuclear localization signals may be provided with or otherwise attached to the RNA guided DNA binding protein or the guide RNA for promoting the movement of the RNA guided DNA binding protein or the guide RNA into the nucleus.

The RNA-guided DNA binding protein is more fully described herein and includes an RNA-guided DNA binding protein nuclease, a thermophilic RNA-guided DNA binding protein nuclease, an RNA-guided DNA binding protein nickase, or a nuclease null RNA-guided DNA binding protein. According to one aspect, the RNA-guided DNA binding protein includes a Cas nuclease, a Cas nickase or a nuclease null Cas protein. A Cas as described herein may be any Cas known to those of skill in the art that may be directed to a target nucleic acid using an RNA as known to those of skill in the art. The Cas may be wild type or a homolog or ortholog thereof, such as Cpf1 (See, Zetsche, Bernd et al., Cpf1 Is a Single RNA-Guided Endonuclease of a Class 2 CRISPR-Cas System, *Cell*, Volume 163, Issue 3, pgs 759-771, hereby incorporated by reference in its entirety) or C2c2 or C2c1 or other RNA guided endonucleases known to those of skill in the art. The Cas may be nonnaturally occurring, such as an engineered Cas as disclosed in Slaymaker, I. M., Gao, L., Zetsche, B., Scott, D. A., Yan, W. X. and Zhang, F., 2016. Rationally engineered Cas9 nucleases with improved specificity. Science, 351(6268), pp. 84-88 hereby incorporated by reference in its entirety. The Cas may have one or more nucleolytic domains altered to prevent nucleolytic activity, such as with a Cas nickase or nuclease null or "dead" Cas. Aspects of the present disclosure utilize nicking to effect cutting of one strand of the target nucleic acid. A nuclease null or "dead" Cas may have a nuclease attached thereto to effect cutting, cleaving or nicking of the target nucleic acid. Such nucleases are known to those of skill in the art.

According to one aspect, the RNA-guided DNA binding protein includes a Cas9 nuclease, a Cas9 nickase or a nuclease null Cas9 protein. According to one aspect, the RNA-guided DNA binding protein includes a spCas9 nuclease, a spCas9 nickase or a nuclease null spCas9 protein. According to one aspect, the RNA-guided DNA binding proteins includes *S. pyogenes* Cas9, *S. thermophilis* Cas9, *N meningitides* Cas9, *T denticola* Cas9, or *S. aureus* Cas9. According to one aspect, the RNA-guided DNA binding protein includes a Cpf1 nuclease, a Cpf1 nickase or a nuclease null Cpf1 protein.

According to one aspect, the RNA-guided DNA binding protein includes an effector moiety or group attached thereto. The RNA-guided DNA binding protein may be a nuclease null RNA-guided DNA binding protein including an effector moiety or group attached thereto. An effector moiety or group includes a modulator moiety or group. Exemplary effector groups or moieties include a detectable moiety, a transcriptional regulator, a protein domain, a nuclease, a phosphatase, deaminase, kinase, polynucleotide kinase, Uracil-DNA glycosylase, nuclease, endonuclease, exonuclease, site-specific nuclease, ligase, polymerase, recombinase, methyl-transferase, fluorescent protein, beta-galactosidase, antibody, scFv single-chain variable fragment of an antibody, nanobody, transcriptional activator, transcriptional repressor, biotin, streptavidin, aptamer, nanoparticle, gold nanoparticle, quantum dot, magnetic bead, paramagnetic particle, or oligonucleotide.

According to one aspect, the guide RNA includes an effector moiety or group attached thereto. An effector moiety or group includes a modulator moiety or group. Exemplary effector groups or moieties include a detectable moiety, a transcriptional regulator, a protein domain, a nuclease, a phosphatase, deaminase, kinase, polynucleotide kinase, Uracil-DNA glycosylase, nuclease, endonuclease, exonuclease, site-specific nuclease, ligase, polymerase, recombinase, methyl-transferase, fluorescent protein, beta-galactosidase, antibody, scFv single-chain variable fragment of an antibody, nanobody, transcriptional activator, transcriptional repressor, biotin, streptavidin, aptamer, nanoparticle, gold nanoparticle, quantum dot, magnetic bead, paramagnetic particle, or oligonucleotide.

According to the methods described herein, the target nucleic acid sequence is modulated, for example by being cut or nicked by the RNA-guided DNA binding protein. A target nucleic acid may be modulated by being bound by the RNA-guided DNA binding protein. A target nucleic acid may be modulated by the function of the effector group or moiety attached to the RNA-guided DNA binding protein or the guide RNA. A target nucleic acid may be modulated by being bound by the RNA-guided DNA binding protein and the function of the effector group or moiety attached to the RNA-guided DNA binding protein or the guide RNA.

Methods described herein can be used to cleave exogenous nucleic acids. Methods described herein can be used to cleave endogenous nucleic acids. Methods described herein can be used with known Cas proteins or orthologs or engineered versions thereof. Methods described herein can be practiced in vivo, ex vivo or in vitro. Methods described herein can be multiplexed within a single target nucleic acid region or across multiple regions.

According to one aspect, the present disclosure provides a method of targeting a nucleic acid in a cell. The method includes providing the cell with a guide RNA sequence including a reverse transcription primer binding site or docking site as described herein, providing the cell with an RNA guided DNA binding protein (or the cell already includes an RNA guided DNA binding protein) as described herein, wherein the guide RNA sequence and the RNA guided DNA binding protein co-localize to the target nucleic acid sequence, the target nucleic acid is modulated or cleaved or nicked as described herein and as known in the art, and the spacer sequence of the guide RNA is sequenced and identified using reverse transcription methods, such as fluorescence in situ sequencing, known to those of skill in the art. According to certain aspects, the target nucleic acid may be repaired by homologous recombination or nonhomologous end joining or other cellular repair mechanisms and may also include a donor nucleic acid sequence which is inserted into the target nucleic acid.

Methods described herein are useful with CRISPR systems which utilize an RNA guided DNA binding protein, such as a Cas protein, and a guide RNA including a spacer sequence, a tracr mate sequence and a tracr sequence. The portion of the guide RNA attached to the 3' nucleotide of the spacer sequence may be referred to as a scaffold sequence. Various scaffold sequences are known to those of skill in the art. According to certain aspects, the Cas protein may be provided to the cell as a native protein. According to certain aspects, the Cas protein may be provided to the cell as a nucleic acid which is expressed by the cell to provide the Cas protein. According to certain aspects, the expression of the Cas protein in the cell is inducible. According to certain aspects, the guide RNA may be provided to the cell as a native guide RNA. According to certain aspects, the guide RNA may be provided to the cell as a nucleic acid which is expressed by the cell to provide the guide RNA. According to one aspect, a plurality of guide RNAs may be provided to the cell wherein the guide RNAs are directed to a plurality of target nucleic acid sequences.

According to still another aspect, the present disclosure is directed to a method of targeting a nucleic acid sequence using an RNA guided DNA binding protein and a guide RNA, such as a CRISPR system, including providing a first foreign nucleic acid encoding a guide RNA sequence including a spacer sequence complementary to a protospacer sequence in the nucleic acid sequence, providing a second foreign nucleic acid encoding an RNA guided DNA binding protein, such as a Cas protein, wherein the guide RNA sequence and the Cas protein are expressed, wherein the guide RNA sequence and the Cas protein co-localize to the nucleic acid sequence and the Cas protein binds or cleaves or nicks or modulates directly or indirectly the nucleic acid sequence in a site specific manner.

According to one aspect, the guide RNA is provided to the cell by introducing into the cell a first foreign nucleic acid encoding the guide RNA, wherein the guide RNA is expressed. According to one aspect, the Cas protein is expressed by the cell. According to one aspect, the Cas protein is naturally occurring within the cell. According to one aspect, the Cas protein is provided to the cell by introducing into the cell a second foreign nucleic acid encoding the Cas protein, wherein the Cas protein is expressed. The Cas protein and the guide RNA co-localize to the target nucleic acid.

According to one aspect, the cell is in vitro, in vivo or ex vivo. According to one aspect, the cell is a eukaryotic cell or prokaryotic cell. According to one aspect, the cell is a bacteria cell, a yeast cell, a fungal cell, a mammalian cell, a human cell, a stem cell, a progenitor cell, a human induced pluripotent stem cell, a plant cell or an animal cell. According to one aspect, the target nucleic acid is genomic DNA, mitochondrial DNA, plasmid DNA, viral DNA, exogenous DNA or cellular RNA.

Various Cas proteins are known to those of skill in the art and include CasI (Cas3), Cas IA (Cas8a), CasIB (Cas8b), CasIC (Cas8c), CasID (Cas10d), CasIE (Cse1), CasIF (Csy1), CasIU, CasII (Cas9), CasIIA (Csn2), CasIIB (Cas4), CasIIC, CasIII (Cas10), CasIIIA (Csm2), CasIIIB (Cmx5), CasIIIC, CasIIID, CasIV (Csf1), CasIVA, CasIVB, and CasV (Cpf1) and the like. Various guide RNA sequences utilized with companion RNA guided DNA binding proteins are known to those of skill in the art. The CRISPR type II system is a recent development that has been efficiently utilized in a broad spectrum of species. See Friedland, A. E., et al., Heritable genome editing in *C. elegans* via a CRISPR-Cas9 system. Nat Methods, 2013. 10(8): p. 741-3, Mali, P., et al., RNA-guided human genome engineering via Cas9. Science, 2013. 339(6121): p. 823-6, Hwang, W. Y., et al., Efficient genome editing in zebrafish using a CRISPR-Cas system. Nat Biotechnol, 2013, Jiang, W., et al., RNA-guided editing of bacterial genomes using CRISPR-Cas systems. Nat Biotechnol, 2013, Jinek, M., et al., RNA-programmed genome editing in human cells. eLife, 2013. 2: p. e00471, Cong, L., et al., Multiplex genome engineering using CRISPR/Cas systems. Science, 2013. 339(6121): p. 819-23, Yin, H., et al., Genome editing with Cas9 in adult mice corrects a disease mutation and phenotype. Nat Biotechnol, 2014. 32(6): p. 551-3. CRISPR is particularly customizable because the active form consists of an invariant Cas9 protein and an easily programmable guide RNA (gRNA). See Jinek, M., et al., A programmable dual-RNA-guided DNA endonuclease in adaptive bacterial immunity. Science, 2012. 337(6096): p. 816-21. Of the various CRISPR orthologs, the *Streptococcus pyogenes* (Sp) CRISPR is the most well-characterized and widely used. The Cas9-gRNA complex first probes DNA for the protospacer-adjacent motif (PAM) sequence (-NGG for Sp Cas9), after which Watson-Crick base-pairing between the gRNA and target DNA proceeds in a ratchet mechanism to form an R-loop. Following formation of a ternary complex of Cas9, gRNA, and target DNA, the Cas9 protein generates two nicks in the target DNA, creating a double-strand break (DSB) that is predominantly repaired by the non-homologous end joining (NHEJ) pathway or, to a lesser extent, template-directed homologous recombination (HR). CRISPR methods are disclosed in U.S. Pat. Nos. 9,023,649 and 8,697,359 and Fu et al., Nature Biotechnology, Vol. 32, Number 3, pp. 279-284 (2014) each of which are hereby incorporated by reference in its entirety. Additional references describing CRISPR-Cas9 systems including nuclease null variants (dCas9) and nuclease null variants functionalized with effector domains such as transcriptional activation domains or repression domains include J. D. Sander and J. K. Joung, *Nature biotechnology* 32 (4), 347 (2014); P. D. Hsu, E. S. Lander, and F. Zhang, *Cell* 157 (6), 1262 (2014); L. S. Qi, M. H. Larson, L. A. Gilbert et al., *Cell* 152 (5), 1173 (2013); P. Mali, J. Aach, P. B. Stranges et al., *Nature biotechnology* 31 (9), 833 (2013); M. L. Maeder, S. J. Linder, V. M. Cascio et al., *Nature methods* 10 (10), 977 (2013); P. Perez-Pinera, D. D. Kocak, C. M. Vockley et al., *Nature methods* 10 (10), 973 (2013); L. A. Gilbert, M. H. Larson, L. Morsut et al., *Cell* 154 (2), 442 (2013); P. Mali, K. M. Esvelt, and G. M. Church, *Nature methods* 10 (10), 957 (2013); and K. M. Esvelt, P. Mali, J. L. Braff et al., *Nature* methods 10 (11), 1116 (2013).

Exemplary RNA-Guided DNA Binding Proteins

RNA guided DNA binding proteins are readily known to those of skill in the art to bind to DNA for various purposes. Such DNA binding proteins may be naturally occurring. DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

In general, bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus* thermophilus. *Journal of Bacteriology* 190, 1390 (February, 2008). Additional useful Cas proteins are from *S. thermophilis* or *S. aureus*.

Three classes of CRISPR systems are generally known and are referred to as Type I, Type II or Type III). According to one aspect, a particular useful enzyme according to the present disclosure to cleave dsDNA is the single effector enzyme, Cas9, common to Type II. See K. S. Makarova et al., Evolution and classification of the CRISPR-Cas systems. *Nature* reviews. *Microbiology* 9, 467 (June, 2011) hereby incorporated by reference in its entirety. Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. TracrRNA-crRNA fusions are contemplated for use in the present methods.

According to one aspect, the enzyme of the present disclosure, such as Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermophilus* Type II systems require NGGNG (see P. Horvath, R. Barrangou, CRISPR/Cas, the immune system of bacteria and archaea. *Science* 327, 167 (Jan. 8, 2010) hereby incorporated by reference in its entirety and NNAGAAW (see H. Deveau et al., Phage response to CRISPR-encoded resistance in Streptococcus thermophilus. *Journal of bacteriology* 190, 1390 (February, 2008) hereby incorporated by reference in its entirety), respectively, while different *S. mutans* systems tolerate NGG or NAAR (see J. R. van der Ploeg, Analysis of CRISPR in Streptococcus mutans suggests frequent occurrence of acquired immunity against infection by M102-like bacteriophages. *Microbiology* 155, 1966 (June, 2009) hereby incorporated by reference in its entirety. Bioinformatic analyses have generated extensive databases of CRISPR loci in a variety of bacteria that may serve to identify additional useful PAMs and expand the set of CRISPR-targetable sequences (see M. Rho, Y. W. Wu, H. Tang, T. G. Doak, Y. Ye, Diverse CRISPRs evolving in human microbiomes. *PLoS genetics* 8, e1002441 (2012) and D. T. Pride et al., Analysis of streptococcal CRISPRs from human saliva reveals substantial sequence diversity within and between subjects over time. *Genome research* 21, 126 (January, 2011) each of which are hereby incorporated by reference in their entireties.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., *Science* 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: Methanococcus maripaludis C7; *Corynebacterium diphtheriae; Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; Thermomonospora curvata DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; Roseiflexus RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua; Lactobacillus casei; Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus* gallolyticus UCN34 uid46061; *Streptococcus gordonii* Challis subst CH1; *Streptococcus mutans* NN2025 uid46353; *Streptococcus mutans; Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus* thermophiles LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum; Mycoplasma* mobile 163K; *Mycoplasma penetrans; Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; Azospirillum B510 uid46085; *Rhodospirillum rubrum* ATCC 11170; Diaphorobacter TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni; Campylobacter lari* RM2100; *Helicobacter hepaticus; Wolinella succinogenes; Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida; Francisella tularensis novicida* U112; *Francisella tularensis holarctica; Francisella tularensis* FSC 198; *Francisella tularensis tularensis; Francisella tularensis* WY96-3418; and *Treponema denticola* ATCC 35405. The Cas9 protein may be referred by one of skill in the art in the literature as Csn1. An exemplary *S. pyogenes* Cas9 protein sequence is provided in Deltcheva et al., *Nature* 471, 602-607 (2011) hereby incorporated by reference in its entirety.

Modification to the Cas9 protein is a representative embodiment of the present disclosure. CRISPR systems useful in the present disclosure are described in R. Barrangou, P. Horvath, CRISPR: new horizons in phage resistance and strain identification. *Annual review of food science and technology* 3, 143 (2012) and B. Wiedenheft, S. H. Sternberg, J. A. Doudna, RNA-guided genetic silencing systems in bacteria and archaea. *Nature* 482, 331 (Feb. 16, 2012) each of which are hereby incorporated by reference in their entireties.

According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase. An exemplary DNA binding protein is an RNA guided DNA binding protein nuclease of a Type II CRISPR System, such as a Cas9 protein or modified Cas9 or homolog of Cas9. An exemplary DNA binding protein is a Cas9 protein nickase. An exemplary DNA binding protein is an RNA guided DNA binding protein of a Type II CRISPR System which lacks nuclease activity. An exemplary DNA binding protein is a nuclease-null or nuclease deficient Cas9 protein.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinek et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 ("Cas9Nuc") and exhibits reduced or eliminated nuclease activity, or nuclease activity is absent or substantially absent within levels of detection. According to this aspect, nuclease activity for a Cas9Nuc may be undetectable using known assays, i.e. below the level of detection of known assays.

According to one aspect, the Cas9 protein, Cas9 protein nickase or nuclease null Cas9 includes homologs and orthologs thereof which retain the ability of the protein to bind to the DNA and be guided by the RNA. According to one aspect, the Cas9 protein includes the sequence as set forth for naturally occurring Cas9 from *S. thermophiles* or *S. pyogenes* or *S. aureus* and protein sequences having at least 30%, 40%, 50%, 60%, 70%, 80%, 90%, 95%, 98% or 99% homology thereto and being a DNA binding protein, such as an RNA guided DNA binding protein.

An exemplary CRISPR system includes the S. thermophiles Cas9 nuclease (ST1 Cas9) (see Esvelt K M, et al., Orthogonal Cas9 proteins for RNA-guided gene regulation and editing, Nature Methods, (2013) hereby incorporated by reference in its entirety). An exemplary CRISPR system includes the *S. pyogenes* Cas9 nuclease (Sp. Cas9), an extremely high-affinity (see Sternberg, S. H., Redding, S., Jinek, M., Greene, E. C. & Doudna, J. A. DNA interrogation by the CRISPR RNA-guided endonuclease Cas9. *Nature* 507, 62-67 (2014) hereby incorporated by reference in its entirety), programmable DNA-binding protein isolated from a type II CRISPR-associated system (see Garneau, J. E. et al. The CRISPR/Cas bacterial immune system cleaves bacteriophage and plasmid DNA. *Nature* 468, 67-71 (2010) and Jinek, M. et al. A programmable dual-RNA-guided DNA endonuclease in adaptive bacterial immunity. *Science* 337, 816-821 (2012) each of which are hereby incorporated by reference in its entirety). According to certain aspects, a nuclease null or nuclease deficient Cas 9 can be used in the methods described herein. Such nuclease null or nuclease deficient Cas9 proteins are described in Gilbert, L. A. et al. CRISPR-mediated modular RNA-guided regulation of transcription in eukaryotes. *Cell* 154, 442-451 (2013); *Mali*, P. et al. CAS9 transcriptional activators for target specificity screening and paired nickases for cooperative genome engineering. *Nature biotechnology* 31, 833-838 (2013); Maeder, M. L. et al. CRISPR RNA-guided activation of endogenous human genes. *Nature methods* 10, 977-979 (2013); and Perez-Pinera, P. et al. RNA-guided gene activation by CRISPR-Cas9-based transcription factors. *Nature methods* 10, 973-976 (2013) each of which are hereby incorporated by reference in its entirety. The DNA locus targeted by Cas9 (and by its nuclease-deficient mutant, "dCas9" precedes a three nucleotide (nt) 5'-NGG-3' "PAM" sequence, and matches a 15-22-nt guide or spacer sequence within a Cas9-bound RNA cofactor, referred to herein and in the art as a guide RNA. Altering this guide RNA is sufficient to target Cas9 or a nuclease deficient Cas9 to a target nucleic acid. In a multitude of CRISPR-based biotechnology applications (see Mali, P., Esvelt, K. M. & Church, G. M. Cas9 as a versatile tool for engineering biology. *Nature methods* 10, 957-963 (2013); Hsu, P. D., Lander, E. S. & Zhang, F. Development and Applications of CRISPR-Cas9 for Genome Engineering. *Cell* 157, 1262-1278 (2014); Chen, B. et al. Dynamic imaging of genomic loci in living human cells by an optimized CRISPR/Cas system. *Cell* 155, 1479-1491 (2013); Shalem, O. et al. Genome-scale CRISPR-Cas9 knockout screening in human cells. *Science* 343, 84-87 (2014); Wang, T., Wei, J. J., Sabatini, D. M. & Lander, E. S. Genetic screens in human cells using the CRISPR-Cas9 system. *Science* 343, 80-84 (2014); Nissim, L., Perli, S. D., Fridkin, A., Perez-Pinera, P. & Lu, T. K. Multiplexed and Programmable Regulation of Gene Networks with an Integrated RNA and CRISPR/Cas Toolkit in Human Cells. *Molecular cell* 54, 698-710 (2014); Ryan, O. W. et al. Selection of chromosomal DNA libraries using a multiplex CRISPR system. *eLife* 3 (2014); Gilbert, L. A. et al. Genome-Scale CRISPR-Mediated Control of Gene Repression and Activation. *Cell* (2014); and Citorik, R. J., Mimee, M. & Lu, T. K. Sequence-specific antimicrobials using efficiently delivered RNA-guided nucleases. *Nature biotechnology* (2014) each of which are hereby incorporated by reference in its entirety), the guide is often presented in a so-called sgRNA (single guide RNA), wherein the two natural Cas9 RNA cofactors (gRNA, i.e. spacer and tracr mate sequence and tracrRNA) are fused via an engineered loop or linker.

According to one aspect, the Cas9 protein is an enzymatically active Cas9 protein, a Cas9 protein wild-type protein, a Cas9 protein nickase or a nuclease null or nuclease deficient Cas9 protein. The Cas may be nonnaturally occurring, such as an engineered Cas. Additional exemplary RNA-guided DNA binding proteins includes Cas9 proteins include Cas9 proteins attached to, bound to or fused with functional proteins such as transcriptional regulators, such as transcriptional activators or repressors, a Fok-domain, such as Fok 1, an aptamer, a binding protein, PP7, MS2 and the like. The nuclease null Cas9 protein and the guide RNA colocalize to the target nucleic acid or the nucleic acid encoding the guide RNA resulting in binding but not cleaving of the target nucleic acid. The activity or transcription of the target nucleic acid is regulated by such binding. The Cas9 protein can further comprise a transcriptional regulator or DNA modifying protein attached thereto. Exemplary transcriptional regulators are known to a skilled in the art and include VPR, VP64, P65 and RTA. Exemplary DNA-modifying enzymes are known to a skilled in the art and include Cytidine deaminases, APOBECs, Fok1, endonucleases and DNases.

Target Nucleic Acids

Target nucleic acid sequences as described herein may be endogenous or exogenous. An endogenous target is one that exists on the genomic (or otherwise endogenous, e.g., mitochondrial) DNA of the host organism in which the system is provided. An exogenous target sequence is one that does not exist on the genomic (or otherwise endogenous, e.g., mitochondrial) DNA of the host organism in which the system is provided. An exogenous target sequence is one that is nonnaturally occurring within the cell and which may be provided as a plasmid introduced to the cell or a transiently transfected DNA element. In an exemplary embodiment, the exogenous target nucleic acid sequence encodes the modified gRNA itself.

Target nucleic acids include any nucleic acid sequence to which a co-localization complex as described herein can be useful to either cut, nick, regulate, identify, influence or otherwise target for other useful purposes using the methods described herein. Target nucleic acids include cellular RNA. Target nucleic acids include cellular DNA. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. Target nucleic acids include DNA that encodes the modified guide RNA. One of skill based on the present disclosure will readily be able to identify or design guide RNAs and Cas9 proteins which co-localize to a DNA including a target nucleic acid. DNA includes genomic DNA, mitochondrial DNA, viral DNA or exogenous DNA.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

Vectors

Vectors are contemplated for use with the methods and constructs described herein. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, doublestranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" or "operatively linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Methods of non-viral delivery of nucleic acids or native DNA binding protein, native guide RNA or other native species include lipofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term native includes the protein, enzyme or guide RNA species itself and not the nucleic acid encoding the species.

Regulatory Elements

Regulatory elements are contemplated for use with the methods and constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)1, the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

Exemplary Guide RNA

Embodiments of the present disclosure are directed to the use of a RNA-guided DNA binding protein/guide RNA system, such as a CRISPR/Cas system and, in particular, a guide RNA which may include one or more of a spacer sequence, a tracr mate sequence and a tracr sequence. The term spacer sequence is understood by those of skill in the art and may include any polynucleotide having sufficient complementarity with a target nucleic acid sequence to hybridize with the target nucleic acid sequence and direct sequence-specific binding of a CRISPR complex to the target sequence. According to certain aspects, an exemplary spacer sequence is between 10 and 30 nucleotides in length. According to certain aspects, an exemplary spacer sequence is between 15 and 25 nucleotides in length. An exemplary spacer sequence is between 18 and 22 nucleotides in length. An exemplary spacer sequence is 20 nucleotides in length.

The guide RNA may be formed from a spacer sequence covalently connected to a tracr mate sequence (which may be referred to as a crRNA) and a separate tracr sequence, wherein the tracr mate sequence is hybridized to a portion of the tracr sequence. According to certain aspects, the tracr mate sequence and the tracr sequence are connected or linked such as by covalent bonds by a linker sequence, which construct may be referred to as a fusion of the tracr mate sequence and the tracr sequence. The guide RNA sequence connected to the spacer sequence may be referred to as a scaffold sequence and may have one or more secondary structures including one or more stem and loop sequences or structures. The linker sequence referred to herein is a sequence of nucleotides, referred to herein as a nucleic acid sequence, which connect the tracr mate sequence and the tracr sequence. Accordingly, a guide RNA may be a unimolecular species (i.e., a crRNA-tracr RNA fusion, often termed an sgRNA). According to one aspect, the linker sequence may include or be a reverse transcription primer binding site sequence or docking site sequence, such that reverse transcription of the spacer sequence can be carried out using methods known to those skilled in the art. According to one aspect, a portion of the scaffold sequence may also be reverse transcribed depending upon the position or location of the reverse transcription primer binding site sequence or docking site sequence within the scaffold sequence.

Tracr mate sequences and tracr sequences and scaffold sequences are known to those of skill in the art, such as those described in US 2014/0356958, and other publications readily available to one of skill. Such tracr mate sequences and tracr sequences may hybridize to each other as separate molecules or they may be linked using methods known to those of skill in the art to form a single molecule or a fusion. According to certain aspects, the tracr mate sequence is between about 17 and about 27 nucleotides in length.

According to certain aspects, the tracr sequence is between about 65 and about 75 nucleotides in length. Linker sequences may also be present at hairpin structures present as part of the scaffold structure and may be referred to as a "loop." According to certain aspects, the linker nucleic acid sequence or loop which lacks a reverse transcription primer binding site may be between about 4 and about 6 nucleotides in length. According to certain aspects, a reverse transcription primer binding site sequence or docking site sequence may be a linker or loop sequence or may be present with or as part of or in addition to the linker or loop sequence or the linker or loop sequence may be the reverse transcription primer binding site sequence or docking site sequence. When the tracr mate and tracr sequences are separate molecules, the reverse transcription primer binding site may be attached to or part of the tracr mate sequence, such as being attached to the 3' end of the tracr mate sequence.

According to certain methods, two or more or a plurality of guide RNAs may be used in the practice of certain embodiments.

According to certain aspects, the guide RNA is between about 10 to about 500 nucleotides. According to one aspect, the guide RNA is between about 20 to about 100 nucleotides. According to certain aspects, the spacer sequence is between about 10 and about 500 nucleotides in length and particularly between about 14 and about 22 nucleotides in length. According to certain aspects, the tracr mate sequence is between about 10 and about 500 nucleotides in length. According to certain aspects, the tracr sequence is between about 10 and about 100 nucleotides in length. According to certain aspects, the linker nucleic acid sequence is between about 4 and about 200 nucleotides in length, and particularly between about 4 and about 100 nucleotides in length.

Exemplary Transcriptional Regulators

According to one aspect, the RNA-guided DNA binding proteins or the guide RNA may include one or more transcriptional regulator proteins or DNA modifying proteins or domains attached, bound, tethered, connected or fused thereto, as effector moieties or groups. According to one aspect, the transcriptional regulator protein or domain is a transcriptional activator. According to one aspect, the transcriptional regulator protein or domain upregulates expression of the target nucleic acid. According to one aspect, the transcriptional regulator protein or domain is a transcriptional repressor. According to one aspect, the transcriptional regulator protein or domain downregulates expression of the target nucleic acid. Transcriptional activators and transcriptional repressors can be readily identified by one of skill in the art based on the present disclosure. Transcriptional regulator proteins or domains which are transcriptional activators include VP16 and VP64 and others readily identifiable by those skilled in the art based on the present disclosure. See Zhang et al., Nature Biotechnology 29, 149-153 (2011) hereby incorporated by reference in its entirety. The Cas9 protein can further comprise a transcriptional regulator or DNA modifying protein attached thereto. Exemplary transcriptional regulators are known to a skilled in the art and include VPR, VP64, P65 and RTA. Exemplary DNA-modifying enzymes are known to a skilled in the art and include Cytidine deaminases, APOBECs, Fok1, endonucleases and DNases. The transcriptional regulatory domains correspond to targeted loci. Accordingly, aspects of the present disclosure include methods and materials for localizing transcriptional regulatory domains to targeted loci of target nucleic acids by fusing, connecting or joining such domains to an RNA-guided DNA binding protein such as Cas or a guide RNA.

Target Nucleic Acid

Target nucleic acids include any nucleic acid sequence to which a co-localization complex as described herein can be useful to either cut, nick or regulate or modulate. Target nucleic acids include nucleic acid sequences, such as genomic nucleic acids, such as genes, capable of being expressed into proteins. For purposes of the present disclosure, a co-localization complex can bind to or otherwise co-localize with the target nucleic acid at or adjacent or near the target nucleic acid and in a manner in which the co-localization complex may have a desired effect on the target nucleic acid. One of skill based on the present disclosure will readily be able to identify or design guide RNAs and Cas9 proteins which co-localize to a target nucleic acid. One of skill will further be able to identify transcriptional regulator proteins or domains which likewise co-localize to a target nucleic acid.

Detectable Domains or Proteins or Labels

According to one aspect, the RNA-guided DNA binding protein or guide RNA may include one or more detectable proteins or domains or labels or markers attached, bound, connected or fused thereto, which can then be detected or imaged to identify the location of the target nucleic acid sequence. Detectable labels or markers can be readily identified by one of skill in the art based on the present disclosure. Aspects of the methods described herein may make use of epitope tags and reporter gene sequences. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, betaglucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

The following examples are set forth as being representative of the present disclosure. These examples are not to be construed as limiting the scope of the present disclosure as these and other equivalent embodiments will be apparent in view of the present disclosure, figures and accompanying claims.

Example I

In Situ Amplification, Detection and Sequencing
Materials and Methods

HEK/293T cells were seeded at 10,000 per well in 96-well polystyrene dishes coated with poly-D-lysine. 12 hours later, each well was transfected with 100 ng of a plasmid DNA packaged with 0.54 of Lipofectamin 2000 reagent (ThermoFisher Scientific) according to the manufacturer protocol. Positive samples received plasmids such as those for Design 1 or Design 2. Negative control samples received a GFP plasmid. 24 hours after transfection, cells were subjected to in situ amplification and detection of the gRNA transcripts.

In situ detection was carried out according to the previously described sequencing in situ sequencing protocol by Lee, J. H. et al. Highly multiplexed subcellular RNA sequencing in situ, Science 343, 1360-1363 (2014) and Lee, J. H. et al. Fluorescent in situ sequencing (FISSEQ) of RNA for gene expression profiling in intact cells and tissues, Nat. Protoc. 10, 442-458 (2015) each of which are hereby incorporated by reference in its entirety.

In brief, cells were fixed using formalin and permeabilized. Reverse-transcription was then carried out using a target-specific primer (5P-tcttctgaaccagactcttgtcattggaaagttggtataagacaacagtg (SEQ ID NO: 1)) in present of aminoallyl-dUTP. Nascent cDNA strands were crosslinked by treatment with BS(PEG)9 (ThermoFisher Scientific) and RNA was degraded by RNaseA and RNaseH treatment. cDNA was circularized using CircLigaseII (Epicentre). Rolling circle amplification (RCA) was carried out with Phi29 polymerase using a target-specific primer (ggtggagcaattccacaacac (SEQ ID NO: 2)) overnight in presence of aminoallyl-dUTP. Nascent amplicons or 'rolonies' were crosslinked by treatment with BS(PEG)9. Target amplicons were labeled with a fluorescent target-specific detection probe (5Cy5-tcttctgaaccagactcttgt (SEQ ID NO: 3)) which recognizes the reverse-transcription primer and nuclei were stained with DAPI. Samples were imaged with a Zeiss Observer.Z1 inverted microscope using a 20× magnification objective in the DAPI and Cy5 channels.

Example II

Engineered Guide RNA Sequence Design and Results

A gRNA-specific in situ amplification assay using methods of FISSEQ was designed to explore targeted detection of gRNAs with a specific reverse transcription (RT) primer. As shown in FIG. 1, a DNA locus expressing a gRNA (purple) under the U6 promoter (brown) is introduced into cells. The construct also contains designed primer binding sites both downstream and upstream of the gRNA in grey-colored regions. A terminator (light brown) is placed after the second primer binding region. Cells containing this locus, and thus expressing its RNA transcript, are fixed for in situ amplification and detection. In the fixed cells, the RNA transcript is reverse-transcribed using a locus-specific RT (reverse-transcription) primer to obtain a cDNA which is then circularized. The circular cDNA is amplified by the rolling circle amplification (RCA) using a second locus-specific RCA primer, producing a concatemerized amplicon that is confined to a small space in the hydrogel matrix of the experiment. The amplicon is then labeled by a fluorescent oligonucleotide.

Figure 2:
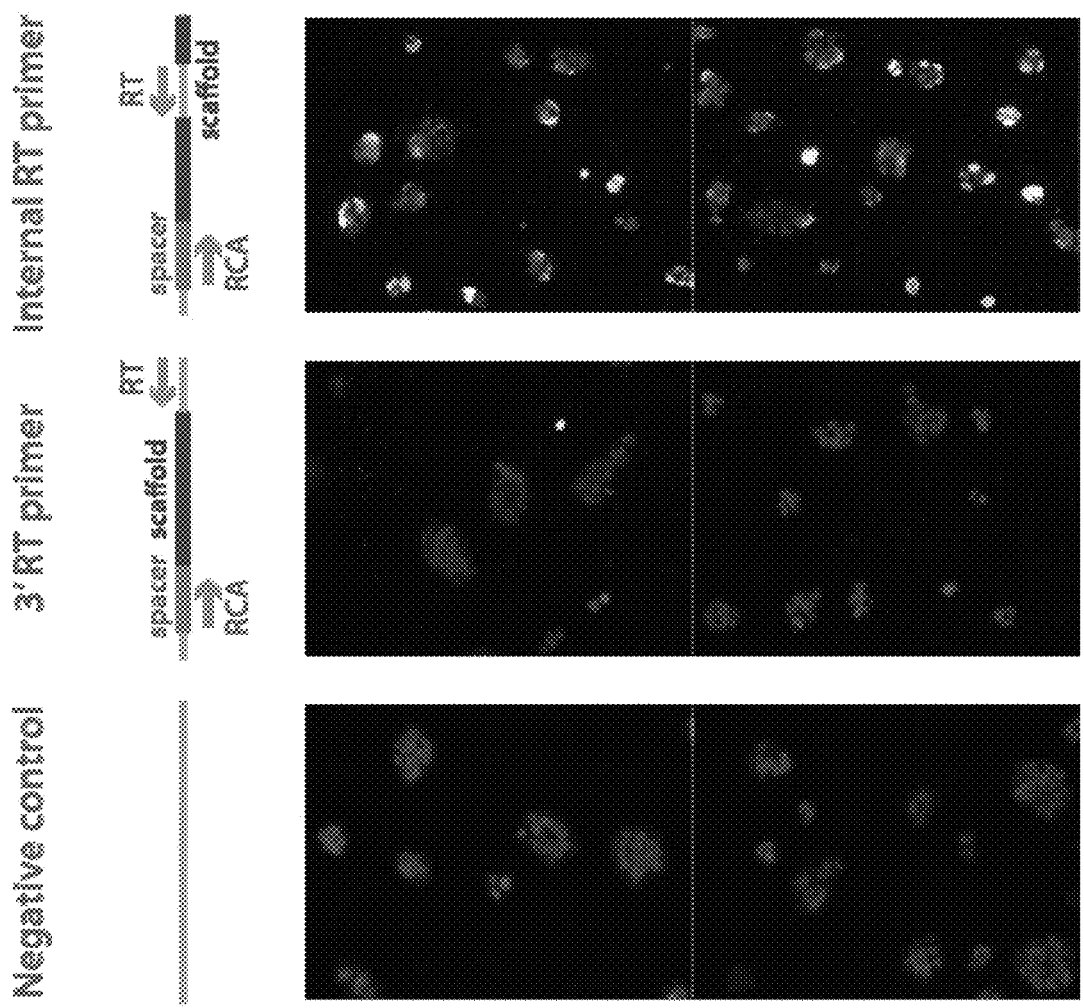
FIG. 2 depicts results of target-specific in situ amplification and detection for two different gRNA constructs and a negative control. The schematic on top shows the position of the reverse-transcription (RT) primer in each design. The bottom panels show a representative field of view from each experimental replicate. Amplicons are labeled with Cy5 (yellow) and nuclei are labeled with DAPI (blue). The amplicon is detectable in a cell transfected with the internal RT primer, whereas placing the RT primer on the 3' end of the gRNA produces very few labeled amplicons, at a level similar to the false positive amplicons in the negative control.

Results of target-specific in situ amplification and detection for two different gRNA constructs and a negative control are depicted in FIG. 2. The schematic on top shows the position of the reverse-transcription (RT) primer in each design. The bottom panels show a representative field of view from each experimental replicate. Amplicons are labeled with Cy5 (yellow) and nuclei are labeled with DAPI (blue). The amplicon is detectable in cells transfected with the internal RT primer, whereas placing the RT primer on the 3' end of the gRNA produces very few labeled amplicons, at a level similar to the false positive amplicons in the negative control.

Using this assay, it was determined that RT primers which bind the native gRNA scaffold sequence do not produce any amplicons. Therefore, the guide RNA was modified to include custom primer docking sites in different positions within the scaffold. When the primer binding site was inserted 3' (downstream) of gRNA scaffold, no amplification was observed (FIG. 2, middle). However, when the RT primer docking site was inserted at a few points in the middle of the scaffold, specific amplification of the gRNA was observed (FIG. 2, right). Therefore, if the primer binding site is inserted proximal to the spacer, scaffolds can be specifically amplified and sequenced in situ (FIG. 2, right). According to one aspect, engineering the guide RNA sequence to include an RT primer binding site or docking site proximate to the spacer sequence reduces the total length of the target cDNA strand (FIG. 1), which facilitates its circularization, circumventing strong secondary structures in the 3' of the gRNA scaffold, and avoiding any secondary structures in an optimal primer docking site which does not naturally exist in the gRNA scaffold.

Figure 3:
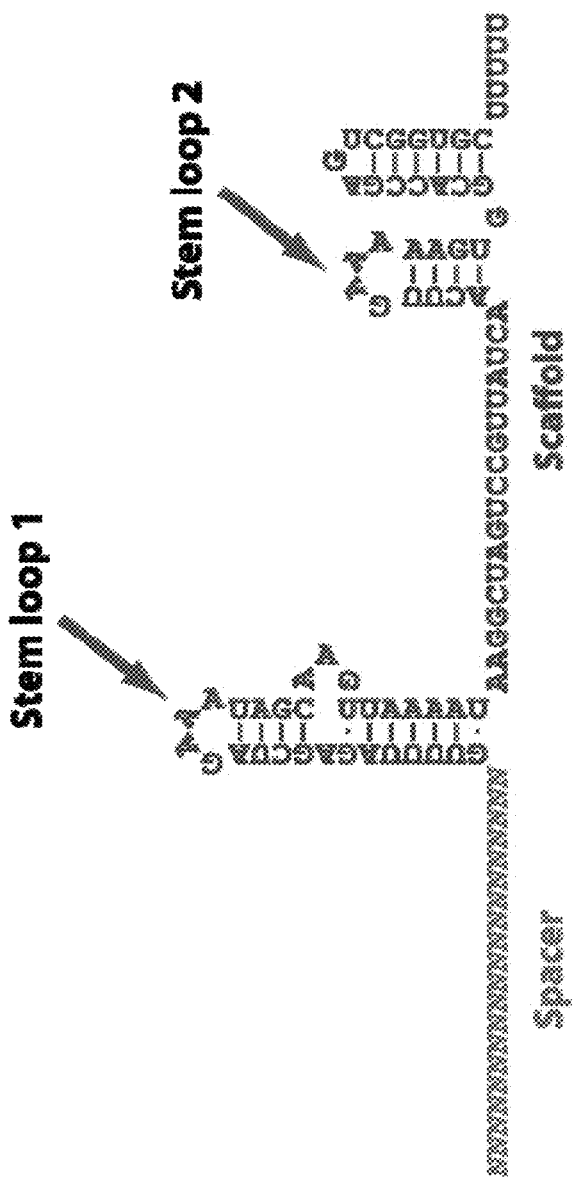
FIG. 3 depicts an exemplary guide RNA sequence (SEQ ID NO: 21) with secondary structure and an indication by arrows marking exemplary locations where a reverse transcription primer binding site sequence or docking site sequence may be located or positioned.

These initial modified gRNA constructs, which have custom primer docking site inserted in the scaffold to enable their detection by FISSEQ, are not functional due to their altered sequence. In order to engineer gRNAs that are not only detectable by FISSEQ but also functional, the RT primer binding site or docking site is inserted into or comprise the loop of a stem loop structure of the scaffold sequence as depicted in FIG. 3 which are tolerant of long insertions. See Konermann, S. et al. Genome-scale transcriptional activation by an engineered CRISPR-Cas9 complex. Nature 517, 583-588 (2015) hereby incorporated by reference in its entirety. Exemplary engineered guide RNA sequences are depicted in FIG. 4 as Design 1 and Design 2. Using a standard traffic light assay and homology recombination repair, the results of which are shown in FIG. 5, it was confirmed that the engineered gRNA sequences maintained their functionality (FIG. 5).

Figure 6:
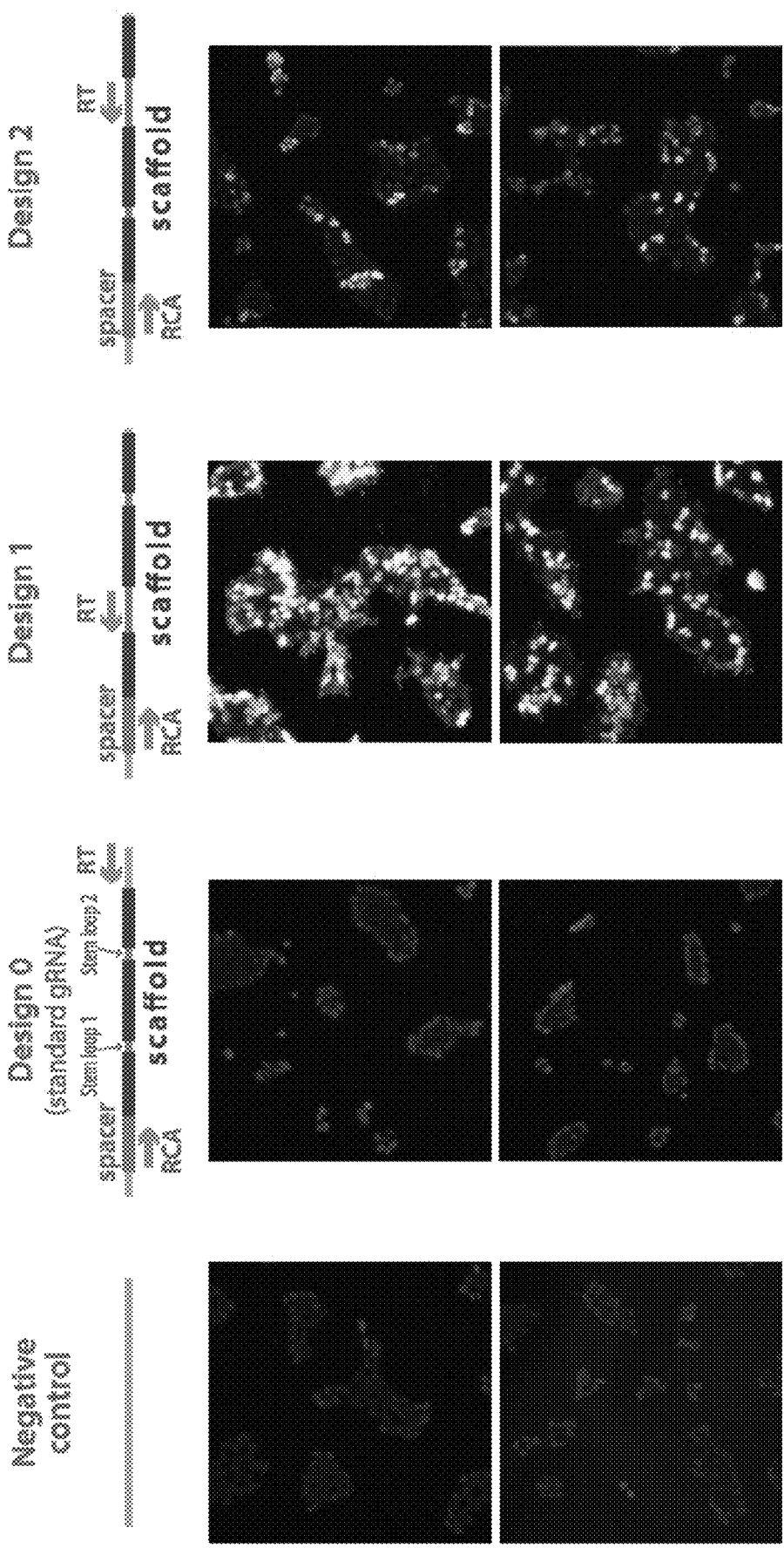
FIG. 6 depicts results of target-specific in situ amplification and detection for engineered functional gRNA designs with inserted RT primer docking site as well as a negative control. The schematic on top shows the position of the reverse-transcription (RT) primer in each design. The bottom panels show a representative field of view from each experimental replicate. Amplicons are labeled with Cy5 (yellow) and nuclei are labeled with DAPI (blue). The amplicon is detectable in cell transfected with the Design 1 or Design 2 constructs, whereas Design 0 shows very few labeled amplicons, at a level similar to the false positive amplicons in the negative control.

Having established the functionality of the engineered guide RNA sequences, the Designs were tested for their suitability for in situ amplification and sequencing, the results of which are shown in FIG. 6. The results show that Design 1 and Design 2 engineered gRNA can be effectively amplified and detected in FISSEQ experiments. Design 1 appears more efficient than design 2, likely due to having a shorter cDNA length and having circumvented more of the gRNA secondary structure.

Example III

Engineered Guide RNA Sequences Maintain Functionality

The functionality of gRNA sequences designed to facilitate targeted detection and or sequencing of gRNA spacer sequences by having a specific reverse transcription (RT) primer was assessed. The performance of such engineered guide RNA sequences were evaluated in the context of homing/self-targeting guide-RNA functionality.

Homing or self-targeting guide RNAs (hgRNAs or stgRNAs) are described in Kalhor et al, 2016, world wide website biorxiv.org/content/early/2016/07/26/055863 posted online with bioRxiv May 27, 2016 entitled Rapidly Evolving Homing CRISPR barcodes, Reza Kalhor, Orashant Mali and George M. Church. These guide RNAs instruct the Cas9-hgRNA complex to target the locus that codes for the hgRNA itself resulting in this locus being mutated through the process of NHEJ repair. If gRNA scaffolds including a reverse transcription primer binding site are functional, the hgRNA versions of the same scaffolds should create mutations in themselves in the presence of a Cas9 protein. Therefore, two homing versions of each of the three gRNA designs in FIG. 4 were constructed. One version—the "a" version—includes a full RT primer docking site inserted into its scaffold. The second version of each design—the "b" version—includes a shortened version of the primer docking site, containing only the first 6 bases of the docking sequence into their scaffolds.

Figure 7:
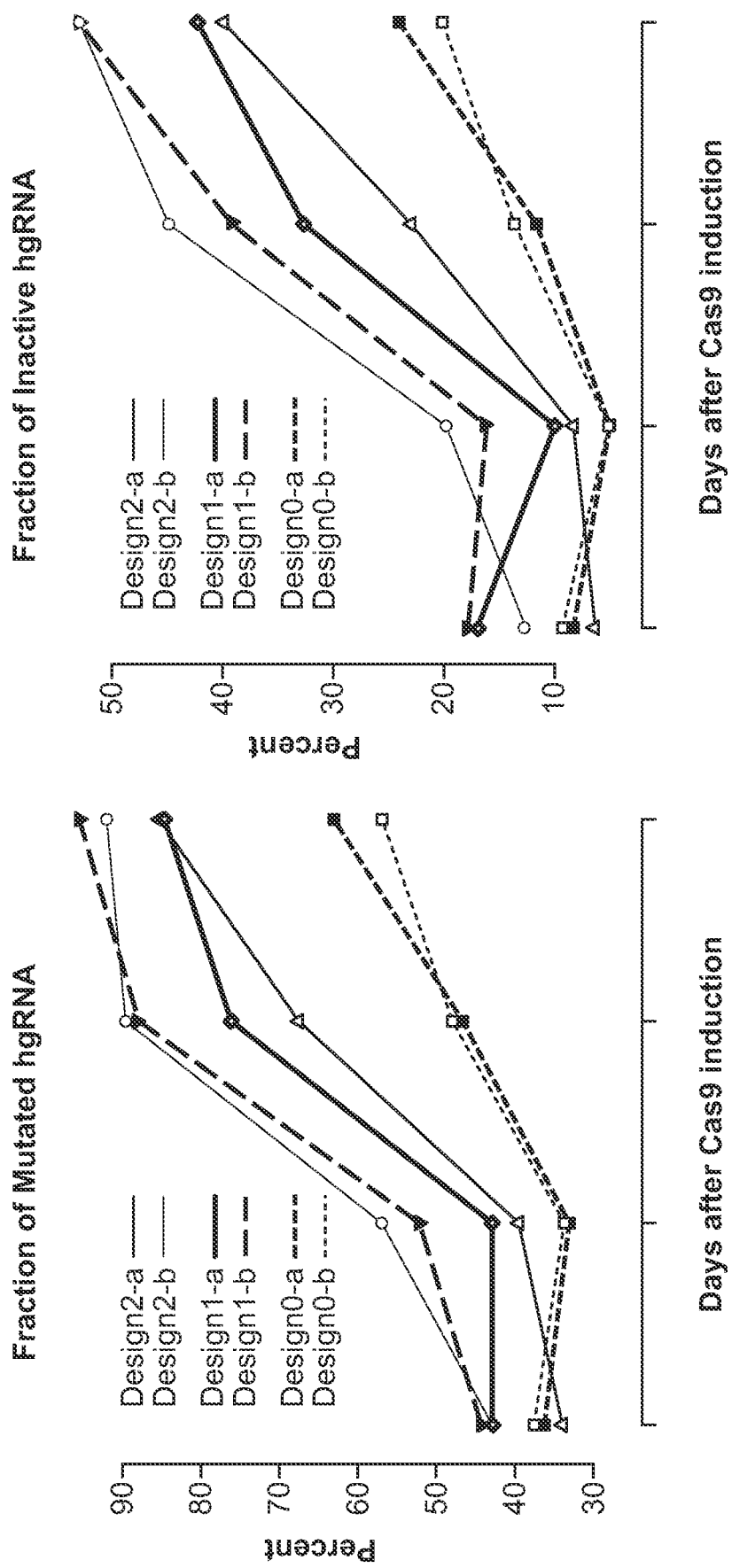
FIG. 7 depicts results indicating that guide RNA sequences engineered to include a reverse transcription primer binding site into or as part of the scaffold sequence are active guide RNA sequences in a homing guide RNA study.

The behavior of these RT-primer site containing hgRNAs was tested by introducing them into cells with an inducible Cas9 protein. Cas9 expression was then induced for 1, 3, or 5 days. The gRNA locus was sequenced at the end of each induction interval (FIG. 7 Left). The gRNA locus sequence/ read that have been altered by the homing gRNA/Cas9 complex and repaired by NHEJ are designated as mutated sequences. The results show that the RT-primer site containing hgRNA loci changed over time with increased abundance of the mutant sequences corresponding to the increased Cas9 protein induction time. During the induction of Cas9 protein, an NHEJ event involving a large deletion that removes the PAM sequence from the gRNA locus eventually happens, thus rendering the hgRNA locus non-functional/inactive as a target (FIG. 7 right). These outcomes indicated that gRNA scaffold designs, which include full or partial RT primer binding sites inserted at their specific Loop1 or Loop2 positions are active in cellular environments and can target desired loci.

Materials and Methods

A clonal HeLa cell line with a genomically integrated, doxycycline-inducible, SP-Cas9 was obtained (HeLa-iSP-Cas9 cells), as described in Kalhor et al, 2016, world wide website biorxiv.org/content/early/2016/07/26/055863 posted online with bioRxiv May 27, 2016 entitled Rapidly Evolving Homing CRISPR barcodes, Reza Kalhor, Orashant Mali and George M. Church.

Six self-targeting guide RNAs (or homing guide RNA or hgRNA), representing the three designs in FIG. 4 under U6 promoter were cloned into a lentiviral vector backbone with Hygromycin resistance gene as a selectable marker (stgRNA1). See Lois C, Hong E J, Pease S, Brown E J, Baltimore D. Germline transmission and tissue-specific expression of transgenes delivered by lentiviral vectors. Science. 2002 Feb. 1; 295(5556):868-72. Epub 2002 Jan. 10. PubMed PMID: 11786607 hereby incorporated by reference in its entirety. These six designs have the following sequences in their hgRNAs:

>Design0-a
GTGGAGCAATTCCACAACACGGGTTAGAGCTAGAAATAGCAAGTTAACCT

AAGGCTAGTCCGTTATCAACTTGAAAAAGTGGCACCGAGTCGGTGCCACT

GTTGTCTTATACCAACTTTCCTTTTTTT (SEQ ID NO: 4)

>Design0-b
GGTGGAGCAATTCCACAACACGTTTAGAGCTAGAAATAGCAAGTTAAAA

TAAGGCTAGTCCGTTATCAACTTGAAAAAGTGGCACCGAGTCGGTGCCAC

TGTTTTTTTT (SEQ ID NO: 5)

>Design1-a
GGTGGAGCAATTCCACAACACGGGTTAGAGCTATAATCACTGTTGTCTTA

TACCAACTTTCCATTATAGCAAGTTAACCTAAGGCTAGTCCGTTATCAAC

TTGAAAAAGTGGCACCGAGTCGGTGCTTTTTTT (SEQ ID NO: 6)

>Design1-b
GGTGGAGCAATTCCACAACACGGGTTAGAGCTATAATCACTGTATTATAG

CAAGTTAACCTAAGGCTAGTCCGTTATCAACTTGAAAAAGTGGCACCGAG

TCGGTGCTTTTTTT (SEQ ID NO: 7)

>Design2-a
GGTGGAGCAATTCCACAACACGGGTTAGAGCTAGAAATAGCAAGTTAACC

TAAGGCTAGTCCGTTATCAACTTATTACACTGTTGTCTTATACCAACTTT

CCTAATAAGTGGCACCGAGTCGGTGCTTTTTTT (SEQ ID NO: 8)

>Design2-b
GGTGGAGCAATTCCACAACACGGGTTAGAGCTAGAAATAGCAAGTTAACC

TAAGGCTAGTCCGTTATCAACTTATTACACTGTTAATAAGTGGCACCGAG

TCGGTGCTTTTTTT (SEQ ID NO: 9)

All the "a" designs contain the complete reverse-transcription primer binding site as in FIG. 4. All the "b" designs have a shortened version of the primer binding site compared to their corresponding "a" designs. These primer binding sites have been boldened and underlined.

A lentiviral virus library carrying each of the above homing guide RNA gene vectors were produced in HEK/293T cells (Design 0-a, Design0-b, Design1-a, Design1-b, Design2-a, and Design2-b hgRNA lentiviral libraries).

HeLa-iSPCas9 cells were transduced separately with each of Design 0-a, Design0-b, Design1-a, Design1-b, Design2-a, and Design2-b hgRNA lentiviral libraries in the presence of 6 microgram/ml polybrene. Two days after transduction, cells were placed under 200 micrograms per milliliter Hygromycin selection and passaged for two days under selection to eliminate the cells that were not transduced with the lentiviral virus, resulting in cell cultures of HeLa-iSPCas9-Design0a-hgRNA, HeLa-iSPCas9-Design0b-hgRNA, HeLa-iSPCas9-Design1a-hgRNA, HeLa-iSPCas9-Design1b-hgRNA, HeLa-iSPCas9-Design2a-hgRNA, and HeLa-iSPCas9-Design2b-hgRNA.

Each HeLa-iSPCas9-Design-hRNA cell line was passaged into a 6-well culture dish. After the cells attached to the bottom of the 6-well culture dish, cells in wells 1 through 4 were respectively induced for 0, 1, 3, and 5 days with 2 μg/ml doxycycline (Dox) to induce SP-Cas9 expression. At the end of each induction time, the cells of the corresponding well were harvested and their genomic DNAs were extracted using Qiagen DNAeasy Blood and Tissue Kit.

For each extracted DNA sample, the hgRNA locus was amplified in a first round of PCR amplification with the following primers:

Forward primer:
    atggactatcatatgcttaccgt  (SEQ ID NO: 10)

Reverse primer:          (SEQ ID NO: 11)
    ctgccatttgtctcgaggtc

PCR was done with initial denaturation of 5 minutes at 95° C., 25 cycles of 95° C. for 30 seconds and 65° C. for 1 minute, and a final extension of 5 minutes at 72° C.

In a second round of PCR amplification, the PCR product from the first round was amplified with NEBNext Indexing Sets 1 and 2. The now-indexed products of this second PCR amplification round were combined into a library for subsequent DNA sequencing. This library was sequenced using Illumina MiSeq platform with 190 bp single-end reads and 8 bp index reads.

Evaluation of sequencing results clearly revealed the activity of these guide RNAs (FIG. 7). Whereas before induction more than 75% of the sequenced hgRNAs match the exact sequence of their design template hgRNA, with increasing induction time length, the hgRNA sequences started changing as the non-homologous end joining repair (NHEJ) repairs the cuts the self-targeting gRNAs have introduced upon their target loci while introducing sequence alterations (mutated sequences). Eventually, in the 5 day induced samples less than 20% of all Design1and Design2 RNAs have their original sequence as in FIG. 7 Left. The type of sequence alterations that are produced involved mostly deletions which are similar to alterations that are known to be a result of NHEJ repair.

From the sequencing results, it was also observed that, after induction, the hgRNA loci underwent multiple cycles of cutting and repairing, the hgRNA locus eventually became inactive as the NHEJ repair process eventually led to a large deletion that encompasses the PAM and/or the hgRNA scaffold (FIG. 7 Right).

Example IV

Embodiments

Aspects of the present disclosure are directed to a functional engineered guide RNA sequence which is reverse transcribable and including a primer binding site for reverse transcription at a location within the functional guide RNA which maintains function of the functional guide RNA and also allows the functional guide RNA to be reverse transcribed. Aspects are also directed to a method of making a functional engineered guide RNA sequence which is reverse transcribable comprising providing a primer binding site for reverse transcription at a location within the functional guide RNA which maintains function of the functional guide RNA and also allows the functional guide RNA to be reverse transcribed.

Aspects of the present disclosure are directed to a functional engineered guide RNA sequence including a spacer sequence and a scaffold sequence, wherein the scaffold sequence includes a nucleic acid sequence for reverse transcription. According to one aspect, the functional engineered guide RNA is a homing guide RNA. According to one aspect, the nucleic acid sequence for reverse transcription is a reverse transcription primer binding site sequence or docking site sequence. According to one aspect, the nucleic acid sequence for reverse transcription is an added nucleic acid sequence for reverse transcription.

According to one aspect, the functional engineered guide RNA sequence includes a scaffold sequence including a tracr mate sequence with the nucleic acid sequence for reverse transcription attached to the tracr mate sequence. According to one aspect, the functional engineered guide RNA sequence includes a scaffold sequence including a tracr mate sequence with the nucleic acid sequence for reverse transcription attached to the 3'-end of the tracr mate sequence. According to one aspect, the functional engineered guide RNA sequence includes a scaffold sequence including a tracr mate sequence and a tracr sequence. According to one aspect, the functional engineered guide RNA sequence includes a scaffold sequence including a tracr mate sequence linked or connected or attached to a tracr sequence. According to one aspect, the functional engineered guide RNA sequence includes a scaffold sequence including a tracr mate sequence linked to a tracr sequence by a linker sequence and wherein the linker sequence comprises the nucleic acid sequence for reverse transcription.

According to one aspect, the scaffold sequence includes one or more stem and loop structures, wherein at least one loop structure of the one or more stem and loop structure comprises a nucleic acid sequence for reverse transcription. According to one aspect, the scaffold sequence includes one or more stem and loop structures, wherein at least one loop structure of the one or more stem and loop structure comprises a reverse transcription primer binding site sequence or docking site sequence. According to one aspect, the scaffold sequence includes one or more stem and loop structures, wherein at least one loop structure of the one or more stem and loop structure is modified to include a nucleic acid sequence for reverse transcription. According to one aspect, the scaffold sequence includes one or more stem and loop structures, wherein at least one loop structure of the one or more stem and loop structure is modified to include a reverse transcription primer binding site sequence or docking site sequence. According to one aspect, the scaffold sequence includes one or more stem and loop structures, wherein one or more loops of the one or more stem and loop structure is modified to include a nucleic acid sequence for reverse transcription. According to one aspect, the scaffold sequence includes one or more stem and loop structures, wherein one or more loops of the one or more stem and loop structure is modified to include a reverse transcription primer binding site sequence or docking site sequence. According to one aspect, the scaffold sequence includes one or more stem and loop structures, wherein at least one loop structure of the one or more stem and loop structure comprises a reverse transcription primer binding site sequence or docking site sequence, wherein the loop structure comprising the reverse transcription primer binding site sequence or docking site sequence is proximate the spacer sequence. According to one aspect, the functional engineered guide RNA sequence has the sequence [spacer]-[tracr mate]-[nucleic acid sequence including or being a nucleic acid sequence for reverse transcription]-[tracr]. According to one aspect, the functional engineered guide RNA sequence has the sequence [spacer]-[tracr mate]-[nucleic acid sequence including or being a reverse transcription primer binding site sequence or docking site sequence]-[tracr]. According to one aspect, the functional engineered guide RNA sequence has the sequence

5'NNNNNNNNNNNNNNNNNNNNNGTTTTAGAGCTA

[nucleic acid sequence including or being a nucleic acid sequence for reverse transcription]

TAGCAAGTTAAAATAAGGCTAGTCCGTTATCAACTTGAAAAAGTGGCACC

GAGTCGGTGC-3' (SEQ ID NOS 12 and 13, respectively).

According to one aspect, the functional engineered guide RNA sequence has the sequence

5'NNNNNNNNNNNNNNNNNNNNNGTTTTAGAGCTA

[nucleic acid sequence including or being a reverse transcription primer binding site sequence or docking site sequence]

TAGCAAGTTAAAATAAGGCTAGTCCGTTATCAACTTGAAAAAGTGGCACC

GAGTCGGTGC-3' (SEQ ID NOS 12 and 13, respectively).

According to one aspect, the functional engineered guide RNA sequence has the sequence

5'NNNNNNNNNNNNNNNNNNNNNNGTTTTAGAGCTAATTA (SEQ ID NO: 14)

CACTGTTGTCTTATACCAACTTTCCTAATTAGCAAGTTAAAATAAGGC

TAGTCCGTTATCAACTTGAAAAAGTGGCACCGAGTCGGTGC-3'.

According to one aspect, the functional engineered guide RNA sequence has the sequence

5'NNNNNNNNNNNNNNNNNNNNNNGTTTTAGAGCTAGAAATAGCAAGTTAAA

ATAAGGCTAGTCCGTTATCAACTT

[nucleic acid sequence including or being a nucleic acid sequence for reverse transcription] AAGTGGCACCGAGTCGGTGC-3' (SEQ ID NOS 15 and 16, respectively). According to one aspect, the functional engineered guide RNA sequence has the sequence

5'NNNNNNNNNNNNNNNNNNNNNNGTTTTAGAGCTAGAAATAGCAAGTTAAA

ATAAGGCTAGTCCGTTATCAACTT

[nucleic acid sequence including or being a reverse transcription primer binding site sequence or docking site sequence]AAGTGGCACCGAGTCGGTGC--3'(SEQ ID NOS 15 and 16, respectively). According to one aspect, the functional engineered guide RNA sequence has the sequence

5'NNNNNNNNNNNNNNNNNNNNNNGTTTTAGAGCTAGAAATAGCAAGTTAAA (SEQ ID NO: 17)

ATAAGGCTAGTCCGTTATCAACTTATTA

CACTGTTGTCTTATACCAACTTTCCTAATAAGTGGCACCGAGTCGGTG

C-3'.

The present disclosure provides a *Streptococcus pyogenes* single guide RNA having at least 40% homology with the sequence 5'NNNNNNNNNNNNNNNNNNNNNNGTTTTAGAGCTA[Linker]TAGCAAGT TAAAATAAGGCTAGTCCGTTATCAACTT[Linker]AAGTGGCACCGAGT CGGTGC-3' (SEQ ID NOS 12, 18 and 16, respectively)

wherein one or more of the linkers includes a reverse transcription primer binding site.

The present disclosure provides a *Streptococcus pyogenes* single guide RNA having the sequence 5'NNNNNNNNNNNNNNNNNNNNNNGTTTTAGAGCTA[Linker]TAGCAAGT TAAAATAAGGCTAGTCCGTTATCAACTT[Linker]AAGTGGCACCGAGT CGGTGC-3' (SEQ ID NOS 12, 18 and 16, respectively)

wherein one or more of the linkers includes a reverse transcription primer binding site. According to one aspect, the *Streptococcus pyogenes* single guide has a modified sequence but still functions with *Streptococcus pyogenes* Cas9 protein. According to one aspect, the *Streptococcus pyogenes* single guide has a sequence with at least 40% homology, 50% homology, 60% homology, 70% homology, 80% homology, 85% homology, 90% homology, 95% homology, 96% homology, 97% homology, 98% homology or 99% homology with sequence 5'NNNNNNNNNNNNNNNNNNNNNNGTTTTAGAGCTA[Linker]TAGCAAGT TAAAATAAGGCTAGTCCGTTATCAACTT[Linker]AAGTGGCACCGAGT CGGTGC-3' (SEQ ID NOS 12, 18 and 16, respectively).

According to one aspect, the reverse transcription primer binding site contains the sequence CACTGTTGTCT-TATACCAAC (SEQ ID NO: 19). According to one aspect, the reverse transcription primer binding site has or includes a sequence with at least 49% homology, 50% homology, 60% homology, 70% homology, 80% homology, 85% homology, 90% homology, 95% homology, 96% homology, 97% homology, 98% homology or 99% homology with sequence CACTGTTGTCTTATACCAAC (SEQ ID NO: 19). According to one aspect, the reverse transcription primer binding site has or includes a sequence with at least 49% homology, 50% homology, 60% homology, 70% homology, 80% homology, 85% homology, 90% homology, 95% homology, 96% homology, 97% homology, 98% homology or 99% homology with sequence CACTGTTGTC (SEQ ID NO: 20).

The present disclosure provides a method of identifying a spacer sequence of a functional guide RNA sequence within a cell including one or more RNA-guided DNA binding proteins including, providing the cell with the functional guide RNA sequence including a scaffold sequence, wherein the scaffold sequence includes a primer binding site for reverse transcription, reverse transcribing the spacer sequence using the primer binding site to produce cDNA, amplifying the cDNA to produce amplicons, and sequencing the amplicons to identify the spacer sequence. According to one aspect, the one or more RNA-guided DNA binding proteins includes an RNA-guided DNA binding protein nuclease. According to one aspect, the one or more RNA-guided DNA binding proteins includes a thermophilic RNA-guided DNA binding protein nuclease. According to one aspect, the one or more RNA-guided DNA binding proteins includes an RNA-guided DNA binding protein nickase. According to one aspect, the one or more RNA-guided DNA binding proteins includes a nuclease null RNA-guided DNA binding protein. According to one aspect, the one or more RNA-guided DNA binding proteins includes a Cas nuclease, a Cas nickase or a nuclease null Cas protein. According to one aspect, the one or more RNA-guided DNA binding proteins includes a Cas9 nuclease, a Cas9 nickase or a nuclease null Cas9 protein. According to one aspect, the one or more RNA-guided DNA binding proteins includes a spCas9 nuclease, a spCas9 nickase or a nuclease null spCas9 protein. According to one aspect, the one or more RNA-guided DNA binding proteins includes *S. pyogenes* Cas9, S. thermophilis Cas9, *N meningitidis* Cas9, *T denticola* Cas9, or *S. aureus* Cas9. According to one aspect, the one or more RNA-guided DNA binding proteins includes a Cpf1 nuclease, a Cpf1 nickase or a nuclease null Cpf1 protein. According to one aspect, the one or more RNA-guided DNA binding proteins includes a nuclease null Cas9 protein having a modulator attached thereto. According to one aspect, the one or more RNA-guided DNA binding proteins includes a nuclease null Cas9 protein having a detectable moiety attached thereto. According to one aspect, the one or more RNA-guided DNA binding proteins includes a nuclease null Cas9 protein having a protein domain attached thereto. According to one aspect, the one or more RNA-guided DNA binding proteins includes a nuclease null Cas9 protein having a nuclease attached thereto. According to one aspect, the one or more RNA-guided DNA binding proteins includes a phosphatase, deaminase, kinase, polynucleotide kinase, Uracil-DNA glycosylase, nuclease, endonuclease, exonuclease, site-specific nuclease, ligase, polymerase, recombinase, methyl-transferase, fluorescent protein, beta-galactosidase, antibody, scFv single-chain variable fragment of an antibody, nanobody, transcriptional activator, transcriptional repressor, biotin, streptavidin, aptamer, nanoparticle, gold nanoparticle, quantum dot, magnetic bead, paramagnetic particle, or oligonucleotide attached thereto.

What is claimed is:

1. An engineered guide RNA sequence comprising a spacer sequence and a guide RNA scaffold sequence, wherein the guide RNA scaffold sequence comprises a reverse transcription primer docking site sequence complementary to a locus specific reverse-transcription primer.

2. The engineered guide RNA sequence of claim 1 wherein the guide RNA scaffold sequence includes a tracr mate sequence with the reverse transcription primer docking site sequence attached to the 3'-end of the tracr mate sequence.

3. The engineered guide RNA sequence of claim 1 wherein the guide RNA scaffold sequence includes a tracr mate sequence linked to a tracr sequence by a linker sequence and wherein the linker sequence comprises the reverse transcription primer docking site sequence.

4. The engineered guide RNA sequence of claim 1, wherein the guide RNA scaffold sequence includes one or more stem and loop structures, wherein at least one loop structure of the one or more stem and loop structures comprises the reverse transcription primer docking site sequence.

5. The engineered guide RNA sequence of claim 1, wherein the reverse transcription primer docking site sequence is proximate to the spacer sequence.

6. The engineered guide RNA sequence of claim 1 comprising a sequence encoded by (SEQ ID NO: 12)
5'NNNNNNNNNNNNNNNNNNNNGTTTTAGAGCTA and a sequence encoded by (SEQ ID NO: 13)
TAGCAAGTTAAAATAAGGCTAGTCCGTTATCAACTTGAAA

AAGTGGCACCGAGTCGGTGC-3'.

7. The guide RNA of claim 1 having the sequence (SEQ ID NO: 14)
5'NNNNNNNNNNNNNNNNNNNNNNGTTTTAGAGCTAATTA

*CACTGTTGTCTTATACCAACTTTCC*TAATTAGCAAGTTAAAATAAGGC

TAGTCCGTTATCAACTTGAAAAAGTGGCACCGAGTCGGTGC-3'

8. The guide RNA of claim 1 having the sequence 5'

NNNNNNNNNNNNNNNNNNNNNNGTTTTAGAGCTAGAAATAGCAAGTTAAAAT

AAGGCTAGTCCGTTATCAACTT a nucleic acid sequence including or being a reverse transcription primer binding site sequence or docking site sequence—AAGTGGCACCGAGTCGGTGC-3' (SEQ ID NOS 15 and 16, respectively).

9. The engineered guide RNA sequence of claim 1 having the sequence encoded by (SEQ ID NO: 17)
5'NNNNNNNNNNNNNNNNNNNNNNGTTTTAGAGCTAGAAATAGCAAGTTAAA

ATAAGGCTAGTCCGTTATCAACTTATTA

*CACTGTTGTCTTATACCAACTTTCC*TAATAAGTGGCACCGAGTCGGTG

C-3'

10. The engineered guide RNA sequence of claim 1, wherein the guide RNA scaffold sequence further includes a poly U tail at the 3' end of the scaffold sequence.

11. The engineered guide RNA sequence of claim 1, wherein the reverse transcription designed primer docking site sequence includes a sequence encoded by a sequence with at least 85% homology with sequence CACTGTTGTCTTATACCAAC (SEQ ID NO: 19).

12. The engineered guide RNA sequence of claim 1, wherein the reverse transcription designed primer docking site sequence includes a sequence encoded by a sequence with at least 85% homology with sequence CACTGTTGTC (SEQ ID NO: 20).

* * * * *

SEQUENCE LISTING

```
<160> NUMBER OF SEQ ID NOS: 22

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcttctgaac cagactcttg tcattggaaa gttggtataa gacaacagtg            50

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtggagcaa ttccacaaca c                                           21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tcttctgaac cagactcttg t                                           21

<210> SEQ ID NO 4
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gtggagcaat tccacaacac gggttagagc tagaaatagc aagttaacct aaggctagtc    60
cgttatcaac ttgaaaaagt ggcaccgagt cggtgccact gttgtcttat accaactttc   120
ctttttt                                                            128

<210> SEQ ID NO 5
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

```
ggtggagcaa ttccacaaca cgttttagag ctagaaatag caagttaaaa taaggctagt      60
ccgttatcaa cttgaaaaag tggcaccgag tcggtgccac tgttttttt                 110
```

<210> SEQ ID NO 6
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
ggtggagcaa ttccacaaca cgggttagag ctataatcac tgttgtctta taccaacttt      60
ccattatagc aagttaacct aaggctagtc cgttatcaac ttgaaaaagt ggcaccgagt     120
cggtgctttt ttt                                                         133
```

<210> SEQ ID NO 7
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
ggtggagcaa ttccacaaca cgggttagag ctataatcac tgtattatag caagttaacc      60
taaggctagt ccgttatcaa cttgaaaaag tggcaccgag tcggtgcttt tttt           114
```

<210> SEQ ID NO 8
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
ggtggagcaa ttccacaaca cgggttagag ctagaaatag caagttaacc taaggctagt      60
ccgttatcaa cttattacac tgttgtctta taccaacttt cctaataagt ggcaccgagt     120
cggtgctttt ttt                                                         133
```

<210> SEQ ID NO 9
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
ggtggagcaa ttccacaaca cgggttagag ctagaaatag caagttaacc taaggctagt      60
ccgttatcaa cttattacac tgttaataag tggcaccgag tcggtgcttt tttt           114
```

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
atggactatc atatgcttac cgt                                          23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgccatttg tctcgaggtc                                              20

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 12
nnnnnnnnnn nnnnnnnnnn gttttagagc ta                                32

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tagcaagtta aaataaggct agtccgttat caacttgaaa aagtggcacc gagtcggtgc  60

<210> SEQ ID NO 14
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 14
nnnnnnnnnn nnnnnnnnnn gttttagagc taattacact gttgtcttat accaactttc  60
ctaattagca agttaaaata aggctagtcc gttatcaact tgaaaaagtg gcaccgagtc  120
ggtgc                                                              125

<210> SEQ ID NO 15
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other
```

```
<400> SEQUENCE: 15
nnnnnnnnnn nnnnnnnnnn gttttagagc tagaaatagc aagttaaaat aaggctagtc    60
cgttatcaac tt                                                        72

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aagtggcacc gagtcggtgc                                                20

<210> SEQ ID NO 17
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 17
nnnnnnnnnn nnnnnnnnnn gttttagagc tagaaatagc aagttaaaat aaggctagtc    60
cgttatcaac ttattacact gttgtcttat accaactttc taataagtg gcaccgagtc    120 ggtgc                                                               125

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tagcaagtta aaataaggct agtccgttat caactt                              36

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
```

```
cactgttgtc ttataccaac                                              20

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cactgttgtc                                                         10

<210> SEQ ID NO 21
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 21
nnnnnnnnnn nnnnnnnnnn guuuuagagc uagaaauagc aaguuaaaau aaggcuaguc   60
cguuaucaac uugaaaaagu ggcaccgagu cggugcuuuu u                      101

<210> SEQ ID NO 22
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 22
nnnnnnnnnn nnnnnnnnnn gttttagagc tagaaatagc aagttaaaat aaggctagtc   60
cgttatcaac ttgaaaaagt ggcaccgagt cggtgccact gttgtcttat accaactttc   120
c                                                                  121
```